United States Patent
Duelo Riu et al.

(10) Patent No.: US 12,194,077 B2
(45) Date of Patent: *Jan. 14, 2025

(54) FUNCTIONAL FOODS COMPRISING DIAMINE OXIDASE AND USES THEREOF

(71) Applicant: DR HEALTHCARE ESPAÑA, S.L., Barcelona (ES)

(72) Inventors: Carlos Duelo Riu, Barcelona (ES); Juan José Duelo Riu, Barcelona (ES)

(73) Assignee: DR HEALTHCARE ESPAÑA, S.L, Barcelona (ES)

( * ) Notice: Subject to any disclaimer, the term of this patent is extended or adjusted under 35 U.S.C. 154(b) by 415 days.

This patent is subject to a terminal disclaimer.

(21) Appl. No.: 17/581,031

(22) Filed: Jan. 21, 2022

(65) Prior Publication Data

US 2022/0143151 A1    May 12, 2022

Related U.S. Application Data

(63) Continuation of application No. 15/488,604, filed on Apr. 17, 2017, now abandoned, which is a continuation of application No. 14/005,072, filed as application No. PCT/IB2012/051253 on Mar. 15, 2012, now abandoned.

(30) Foreign Application Priority Data

Mar. 18, 2011 (ES) .............................. ES201130382

(51) Int. Cl.
| | |
|---|---|
| *A61K 9/00* | (2006.01) |
| *A23C 9/12* | (2006.01) |
| *A23C 11/10* | (2021.01) |
| *A23L 2/02* | (2006.01) |
| *A23L 2/52* | (2006.01) |
| *A23L 11/65* | (2021.01) |
| *A23L 33/115* | (2016.01) |
| *A23L 33/17* | (2016.01) |
| *A23L 33/18* | (2016.01) |
| *A61K 38/44* | (2006.01) |
| *A61P 25/28* | (2006.01) |
| *A61K 9/16* | (2006.01) |

(52) U.S. Cl.
CPC ............ *A61K 38/44* (2013.01); *A23C 9/1213* (2013.01); *A23C 11/103* (2013.01); *A23L 2/02* (2013.01); *A23L 2/52* (2013.01); *A23L 11/65* (2021.01); *A23L 33/115* (2016.08); *A23L 33/17* (2016.08); *A23L 33/18* (2016.08); *A61K 9/0056* (2013.01); *A61K 9/0095* (2013.01); *C12Y 104/03006* (2013.01); *C12Y 104/03022* (2013.01); *A23C 2210/40* (2013.01); *A23V 2002/00* (2013.01); *A61K 9/1623* (2013.01)

(58) Field of Classification Search
CPC .......... A61P 25/00; A61P 25/28; A61P 25/06; A61K 9/0095; A61K 9/0053
See application file for complete search history.

*Primary Examiner* — Tracy Liu
(74) *Attorney, Agent, or Firm* — Shackelford, McKinley & Norton, LLP

(57) ABSTRACT

The present invention relates to functional foods comprising DAO and their use for the prevention or treatment of diseases or pathological conditions associated with high levels of histamine in blood, in particular for the prevention or treatment of migraine, chronic fatigue, fibromyalgia, spondylitis and pain caused by muscle contractures.

9 Claims, No Drawings

FUNCTIONAL FOODS COMPRISING DIAMINE OXIDASE AND USES THEREOF

CROSS-REFERENCE TO RELATED APPLICATIONS

This patent application is a continuation application of U.S. patent application Ser. No. 15/488,604. U.S. patent application Ser. No. 15/488,604 is a continuation application of U.S. patent application Ser. No. 14/005,072. U.S. patent application Ser. No. 14/005,072 is a national-stage filing of International Patent Application No. PCT/IB2012/051253, filed on Mar. 15, 2012. International Patent Application No. PCT/IB2012/051253 claims priority from Spanish Application P201130382, filed on Mar. 18, 2011. U.S. patent application Ser. No. 15/488,604, U.S. patent application Ser. No. 14/005,072, International Patent Application No. PCT/IB2012/051253, and Spanish Application P201130382 are incorporated herein by reference.

FIELD OF THE INVENTION

The present invention relates to functional foods comprising diamine oxidase (DAO) for the treatment or prevention of diseases or pathological conditions associated with high histamine levels in blood, in particular for the treatment or prevention of migraine, chronic fatigue, fibromyalgia, spondylitis and pain caused by muscle contractures.

Background of the Invention

Histamine [2 (4-imidazolyl)-ethylamine] is an important mediator in many biological processes including inflammation, gastric acid secretion, neuromodulation and immune function regulation. Because of its potent pharmacological activity, even at very low concentrations, it is necessary to carefully regulate the synthesis, transport, storage, release and degradation of histamine to prevent undesirable reactions. High concentrations of free histamine in the circulation trigger unwanted effects such as headaches, blocked-up nose or rhinorrhoea, respiratory tract obstructions, tachycardia, gastric and intestinal disorders, swelling of eyelids, skin rashes, low blood pressure, bronchospasm, etc.

Histamine is produced by the human body and stored in an inactive form in the metachromatic granules of mast cells and basophil leukocytes, where it is available for immediate release. The highest concentrations of histamine are measured in the lung. After release, histamine becomes an extraordinarily potent mediator of a number of physiological and pathophysiological processes, often also through interaction with cytokines.

Histamine can also enter the body from the outside, since it is generated by microbiological action in the course of the processing of food and therefore is present in substantial quantities in many food-types and fermented beverages such as cheese, wine, canned fish and sauerkraut.

Histamine is formed by decarboxylation of the L-histidine amino acid in a reaction catalyzed by the histidine decarboxylase enzyme (HDC). The main routes of histamine inactivation in mammals are methylation of the imidazole ring, catalyzed by histamine-N-methyltransferase (NMT) to obtain N-methylhistamine, and the oxidative deamination of the primary amino group, catalyzed by diamine oxidase (DAO) to obtain imidazole acetaldehyde.

Both ways of degradation are essential to the organism: DAO eliminates histamine, which, for example, has been absorbed through the food in the intestinal tract and NMT controls the transmission of histaminergic signals in the nervous system.

The main function of DAO is to prevent histamine ingested through food from reaching the bloodstream from the intestine.

In addition to histamine, DAO can degrade other biogenic amines, such as putrescine, spermidine and cadaverine. It has a molecular weight of approximately 182 kDa and a carbohydrate ratio of 11%. It belongs to the type of copper-containing amine oxidases which catalyze the oxidative deamination of primary amines to obtain aldehydes, ammonia and hydrogen peroxide. DAO uses molecular oxygen to oxidatively deaminate histamine to imidazole acetaldehyde, ammonia and hydrogen peroxide.

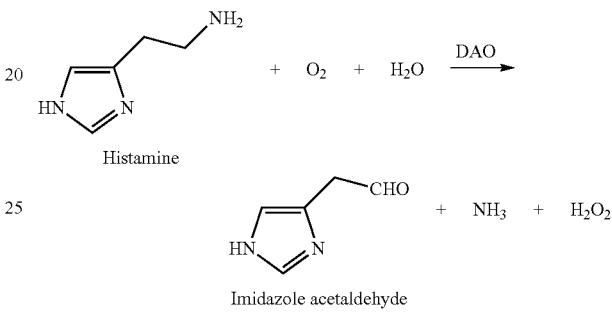

DAO is found mainly in the small intestine, liver, kidneys and blood leukocytes. Pregnant women have a DAO level in blood about 500 to 1000 times higher than non-pregnant women, because DAO is additionally formed in the placenta. Histamine is produced continuously in humans and is excreted via the intestine, being degraded as it passes through the intestinal mucosa by DAO existing there.

DAO is a sensitive enzyme which can be inhibited by various substances, such as other biogenic amines, alcohol and its acetaldehyde degradation product, as well as by various medications.

DAO deficiency has been associated as a possible migraine trigger factor, a condition prevailing in women. An excess of histamine in the body due to lack of DAO, increases the risk of migraine.

EP 132674 discloses a process for the enzymatic separation of free amines of food with a high content thereof, such as chocolate, cheese—especially matured cheese-, salami, wine and yeast extracts using amino oxidase enzymes, in particular DAO, obtained from *Aspergillus niger* organisms in the presence of molecular oxygen. The presence of these free amines in certain foods is considered to cause migraines.

U.S. Pat. No. 4,725,540 discloses a process for the preparation of DAO from a DAO-producing microorganism such as *Candida crusei* or lactic acid-producing bacteria in a nutrient medium, so that the produced DAO is capable of degrading the histamine to a pH between neutral and about 4.

The availability of new foods with health benefits is introduced in the 60s. Since then new types of food designed for gluten-free, low-sodium, low-calorie diets, etc. have emerged on the market. This food is also known as "Functional food", including any food in a natural or processed form which in addition to its nutritional components contains additional components that promote a person's health, physical ability and mental condition. Its description as functional relates to the bromatological concept of "functional property", i.e. the characteristic of a certain food that has shown to have a beneficial effect on one or more specific body functions, without reference to its nutritional value. Thus, it is relevant to health and welfare and helps to reduce the risk of a given disease.

The United States is one of the countries where functional foods are more solidly established intended for the prevention of diseases in the population, such as cereal bars intended for middle-aged women supplemented with calcium to prevent osteoporosis, or protein soya to reduce the risk of breast cancer, or folic acid for a healthier heart, or energy biscuits containing protein, zinc and antioxidants.

In Europe various functional foods with different therapeutic purposes are also known, such as:
- Eggs enriched with omega-3 essential fatty acids, which help reduce the risk of heart disease.
- Milk and yogurt fermented with probiotic cultures to help digestion.
- Cereals with folic acid to help reduce the number of children born with spina bifida.
- Margarines with phytosterols that reduce cholesterol and decrease the risk of heart disease.

Patent application EP 865737 discloses dairy-based foods enriched with a balanced mixture of soluble and insoluble calcium salts.

Patent application WO 9631130 discloses beverage concentrates which comprise a source of calcium and vitamin D.

Patent application WO 9207475 discloses a salad dressing product in the form of an oil emulsion containing a source of calcium.

U.S. application 4851243 discloses calcium-enriched dairy products in the form of a stable suspension.

However, functional foods comprising DAO to help prevent or treat diseases and conditions associated with high histamine levels in blood are not known.

Definitions

"Functional food" (in the literature often abbreviated as FF) is food prepared not only for its nutritional properties but also to fulfil a specific function such as to improve health and reduce the risk of disease. To this end, biologically active components are added such as minerals, vitamins, fatty acids, dietary fibre and antioxidants, etc. This operation of adding exogenous nutrients is also called fortification. This type of food is an emerging field of food science with ample possibilities in food research. Some of the achievements listed in the scientific literature and marketing of food products are the improvement of gastrointestinal functions, the contribution of redox and antioxidant systems, as well as the modification of the macronutrient metabolism. This type of food covers a wide spectrum of possibilities that can range from just cereals and their derivatives to all kinds of dairy products.

"Non-plant origin" refers to all DAO not derived from plants but from animal organisms or other non-plant organisms. Thus, this definition covers all isolated DAO from living organisms.

"Plant origin" means all DAO obtained from plant organisms.

"Biotechnological origin" means all DAO recombinantly prepared in cell culture or in non-plant organisms of any type isolating the DNA for DAO.

In the present invention, "prevention" means preventing the onset of a disease or pathological condition associated with a high level of histamine in blood and characterized by pain increase, including migraine, chronic fatigue, fibromyalgia, spondylitis and muscle contractures.

In the present invention, "treatment" means clinical intervention in an attempt to alter the natural evolution of the individual and is performed during the course of clinical pathology. The desired effects of treatment include prevention of disease recurrence, symptom relief, reduction of any direct or indirect pathological consequence of the disease, decreased rate of progression of the disease, improvement or partial cure of the pathological condition and remission or improved prognosis.

SUMMARY OF THE INVENTION

The problem to be solved by the present invention is the absence of functional foods comprising DAO which would allow prevention or treatment of diseases or pathological conditions associated with high histamine levels in blood. In particular these diseases are migraine, chronic fatigue, fibromyalgia, spondylitis and pain caused by muscle contractures.

This food can be any type of dairy product. The dairy product may be yogurt, milky beverages, a confectionery product, ice-cream or any other beverage such as juice for instance. It can also be any dairy substitute such as soya, oat, almond or rice milk, etc.

This food can also be any type of cereal, muesli or the like. DAO can also be added to vegetable oils, animal and vegetable fats, butter, margarine, etc.

DAO can be added to foods in free form, in the form of powder, lyophilized powder, microgranules, microcapsules, nanocapsules or liposomes.

DAO in the aforementioned forms can also be added to nutritional supplements such as capsules comprising omega-3 fatty acids, vitamins, minerals, amino acids, etc.

DETAILED DESCRIPTION OF THE INVENTION

The present invention relates to a functional food comprising DAO.

One embodiment of the present invention is a dairy-type functional food comprising DAO in free form, in the form of powder, lyophilized powder, microgranules, microcapsules, nanocapsules or liposomes.

Another embodiment of functional food is dairy substitutes such as soya, oat, almond or rice milk, etc. comprising DAO in free form, in the form of powder, lyophilized powder, microgranules, microcapsules, nanocapsules or liposomes.

Functional foods comprising cereal and the like comprising DAO in free form, in the form of powder, lyophilized powder, microgranules, microcapsules, nanocapsules or liposomes also constitute another embodiment of the present invention.

Incorporating DAO in free form, in the form of powder, lyophilized powder, microgranules, microcapsules, nanocapsules or liposomes into food and vitamin supplements is also considered as another object of the present invention.

DAO concentrations in these foods are between 0.01 and 5% by weight of DAO as regards to the total weight of the food, preferably between 0.5 and 1%.

DAO used in the present invention may be either of a biotechnological origin or a plant or animal extraction.

DAO used in the present invention may have a gastrointestinal protection to prevent its degradation in the stomach.

The enteric coating layer covering the microgranules disintegrates or dissolves rapidly in a neutral or alkaline medium.

Microgranule cores can be inert with a sugar or similar base onto which DAO is applied or said cores may already contain DAO mixed with other excipients. Said excipients may be binders, surfactants, fillers, disintegrants, alkaline additives or other pharmaceutically acceptable ingredients alone or in a mixture. The binders may be cellulose type such as hydroxypropylmethylcellulose, hydroxypropylcellulose and carboxymethylcellulose sodium, polyvinylpyrrolidone, sugars, starches and other pharmaceutically acceptable substances based on their cohesive properties. Suitable surfactants are found in the groups of acceptable non-ionic or ionic surfactants, such as for example sodium lauryl sulphate.

Alternatively, DAO can be mixed with alkaline compounds and be further mixed with suitable constituents to be formulated into a core material. Said core materials may be produced by extrusion/spheronization or compression using different process equipment.

DAO can also be mixed with pharmaceutically acceptable alkali salts such as phosphoric acid salts and sodium, potassium, calcium, magnesium and aluminium, carbonic acid, citric acid or other suitably weak organic or inorganic acids; a coprecipitate of aluminium hydroxide/sodium bicarbonate; substances normally used in antiacid preparations such as aluminium, calcium and magnesium hydroxide, magnesium oxide or composite substances, such as $Al_2O_3 \cdot 6MgO \cdot CO_2 \cdot 12H_2O$, $(Mg_6Al_2(OH)_{16}CO3 \cdot 4H_2O$, $MgO \cdot Al_2O_3 \cdot 2SiO_2 \cdot nH_2O$ or similar compounds; pH buffering substances such as trihydroxymethylaminomethane, basic amino acids and their salts or other pharmaceutically acceptable pH buffer substances.

The enteric coating layers may contain pharmaceutically acceptable plasticizers to obtain the desired mechanical properties of flexibility and hardness. These plasticizers may be, for example, triacetin, citric acid esters, phthalic acid esters, cetyl alcohol, polyethylene glycols, polysorbates or other plasticizers.

The microgranules are added to solid functional foods just by mixing and to liquid foods by shaking them together so they remain in suspension.

The present invention also relates to the use of functional food comprising DAO of this invention for the prevention or treatment of diseases or pathological conditions associated with high histamine levels in blood.

The present invention also relates to the use of the functional food comprising DAO of this invention for the prevention or treatment of migraine.

The present invention also relates to the use of functional food comprising DAO of this invention for the prevention or treatment of chronic fatigue, fibromyalgia, spondylitis and pain from muscle contractures.

Furthermore, the present invention also relates to a functional food comprising DAO for use in the prevention or treatment of diseases or pathological conditions associated with high histamine levels in blood. The present invention also relates to a functional food comprising DAO for use in the prevention or treatment of migraine. The present invention also relates to a functional food comprising DAO for the prevention or treatment of chronic fatigue, fibromyalgia, spondylitis and pain caused by muscle contractures.

The present invention also relates to the use of DAO for the manufacture of a functional food according to any of the embodiments of the present invention for the prevention or treatment of diseases or pathological conditions associated with high histamine levels in blood. In particular the disease or pathological condition is migraine, chronic fatigue, fibromyalgia, spondylitis and pain caused by muscle contractures.

EXAMPLES

The following examples further illustrate the present invention.

Example 1

Microgranules are prepared containing 4% of DAO, according to the following formula

| DAO | 4 mg |
| Manitol | 40 mg |
| Microcrystalline cellulose | 25 mg |
| Hydroxypropyl cellulose | 10 mg |
| Corn starch | 10 mg |
| Citric acid | 6 mg |

The microgranules are coated with hydroxypropyl methylcellulose.

Example 2

The following skimmed milk suspension containing DAO is prepared:
A. 10 g of microgranules containing 10% of DAO
B. A dispersion of 2.5 g of gum arabic in 100 g of water and thoroughly hydrated
C. 830 g of skimmed milk prepared with skimmed milk powder
D. 0.15 g of kappa carrageenan The pH of the final product is adjusted to 6.6 to 7.0, UHT sterilized and homogenised. The milk was stable showing no sedimentation during storage from 2° C. up to room temperature.

Example 3

The following almond milk suspension containing DAO is prepared:
A. 15 g of microgranules containing 10% of DAO
B. A dispersion of 2.5 g of gum arabic in 100 g of water and thoroughly hydrated
C. 830 g of almond milk made from almond milk powder
D. 0.15 g of kappa carrageenan The pH of the final product is adjusted to 6.6 to 7.0, UHT sterilized and homogenised. The milk was stable showing no sedimentation during storage from 2° C. up to room temperature.

Example 4

A food supplement is prepared in capsule form incorporating the DAO microgranules of Example 1. For a 350-mg capsule:
A. 25 mg of microgranules containing 10% of DAO
B. 125 mg of fish oil powder containing 20% of omega-3 fatty acid
C. 1.25 mg of vitamin PP (niacin)
D. 5 mg of magnesium stearate
E. 93.75 mg of Emcocel®

Example 5

A vegetable beverage containing DAO microgranules is prepared with the following components:

A. 1.5 g of microgranules containing 10% of DAO
B. 1 g of stabilizer (mixture of pectin, guar and carob seed flour 1:1:1)
C. 70 g of fibrous substance from vegetables (mainly tomatoes)
D. 100 g of mashed vegetables made with tomatoes and carrots
E. 50 g of vegetable juice concentrate (tomato, pepper, celery and beetroot)
F. 90 g of fructose syrup
G. 20 g of lactic-fermented concentrate
H. 2 g of natural vegetable and spice flavouring All components are completed to 600 g with water and mixed. Then homogenized with stirring, degassed and filled into bottles.

Example 7

The functional foods comprising DAO, which are an object of the present invention, are administered to a total of 48 subjects (20 men and 28 women, aged between 23 and 65), the administering protocol being once daily for 4 weeks. These patients were additionally given a diet rich in high-histamine-content foods (cheeses, chocolates, canned fish, etc.). In parallel histamine levels in blood were measured in a group of 30 subjects who were given the same diet yet based on food without any DAO content.

To verify the influence of food comprising DAO in the histamine levels in blood, analyses on histamine levels before and after a 4-week period of food intake were conducted. Values of histamine in blood were considered normal when between 2 and 20 micrograms of histamine per decilitre of blood. Values of histamine in blood were considered high when greater than 20 micrograms of histamine per decilitre of blood.

|  | Subjects given food with DAO: 48 | Subjects not given food with DAO: 30 |
| --- | --- | --- |
| Histamine level in blood | 2-20 micrograms/0.1 L | >>20 micrograms/0.1 L |

The invention claimed is:

1. A method of treating migraine, comprising administering a functional food comprising DAO to a patient, wherein the patient is suffering from migraine, and wherein the DAO is present in a percentage comprised between 0.01% and 1% by weight of DAO relative to the total weight of the functional food, and wherein the treatment is characterized by an effect selected from the group consisting of migraine symptom relief, reduction of any direct or indirect pathological consequence of the migraine, decreased rate of progression of the migraine, improvement of the migraine, or combinations thereof.

2. The method according to claim 1, wherein the DAO is obtained from either a biotechnological origin or a plant or animal extraction.

3. The method according to claim 1, wherein the DAO is gastrointestinal protected.

4. The method according to claim 1, the functional food is a dairy-based product, a non-dairy-based product, or a cereal.

5. The method according to claim 4, wherein the dairy-based product is selected from the group consisting of yogurt, milky beverages, a confectionery product, and ice-cream.

6. The method according to claim 4, wherein the non-dairy based product is selected from the group consisting of juice, soya, oat, almond milk, and rice milk.

7. The method according to claim 1, wherein the functional food is a nutritional or vitamin supplement.

8. The method according to claim 1, wherein the DAO is in the form of microcapsules or nanocapsules.

9. The method according to claim 1, wherein the administering reduces the blood histamine level in the patient to levels between 2 and 20 μg/0.1 L.

* * * * *